_US005692759A_

United States Patent [19]
Flynn

[11] Patent Number: 5,692,759
[45] Date of Patent: Dec. 2, 1997

[54] KEYLESS CHUCK OPERATION DEVICE

[75] Inventor: Jerome R. Flynn, Irvine, Calif.

[73] Assignee: Synergy Medical Products, Inc., Newport Beach, Calif.

[21] Appl. No.: 558,470

[22] Filed: Nov. 16, 1995

Related U.S. Application Data

[63] Continuation-in-part of Ser. No. 229,437, Apr. 12, 1994, abandoned.

[51] Int. Cl.$^6$ .................................................. B23B 31/12
[52] U.S. Cl. ........................... 279/147; 279/60; 279/902
[58] Field of Search ........................... 279/147, 150, 279/902, 60–65

[56] References Cited

U.S. PATENT DOCUMENTS

| | | | |
|---|---|---|---|
| 4,323,324 | 4/1982 | Eberhardt | 279/147 |
| 4,844,488 | 7/1989 | Flynn | 279/147 |
| 5,197,749 | 3/1993 | Moore et al. | 279/147 |

Primary Examiner—Steven C. Bishop
Attorney, Agent, or Firm—Lynn & Lynn

[57] ABSTRACT

A main body formed generally as a hollow cylinder has an open end sized to receive a chuck head into the main body. An outer shell formed generally as a hollow cylinder is mounted to the main body. A gear drive assembly is mounted to the main body and engaged with the face gear of the chuck. The outer shell is selectively manually engagable with the outer shell via a the gear drive assembly such that rotating the chuck head opens or closes the jaws of the chuck, depending upon the direction of rotation. The outer shell has a free wheeling position in which a person may grasp the outer shell and hold it to guide the drill without causing the chuck jaws to tend to open or close.

23 Claims, 15 Drawing Sheets

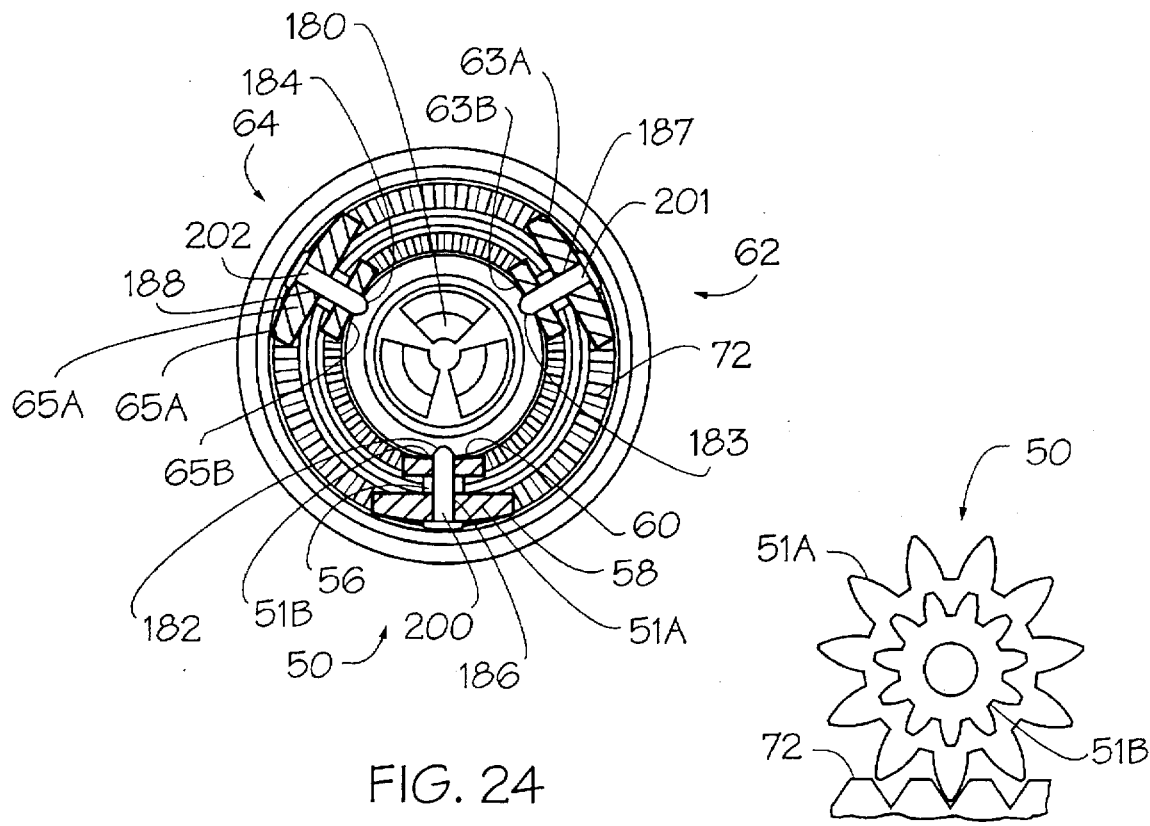
FIG. 24
FIG. 15
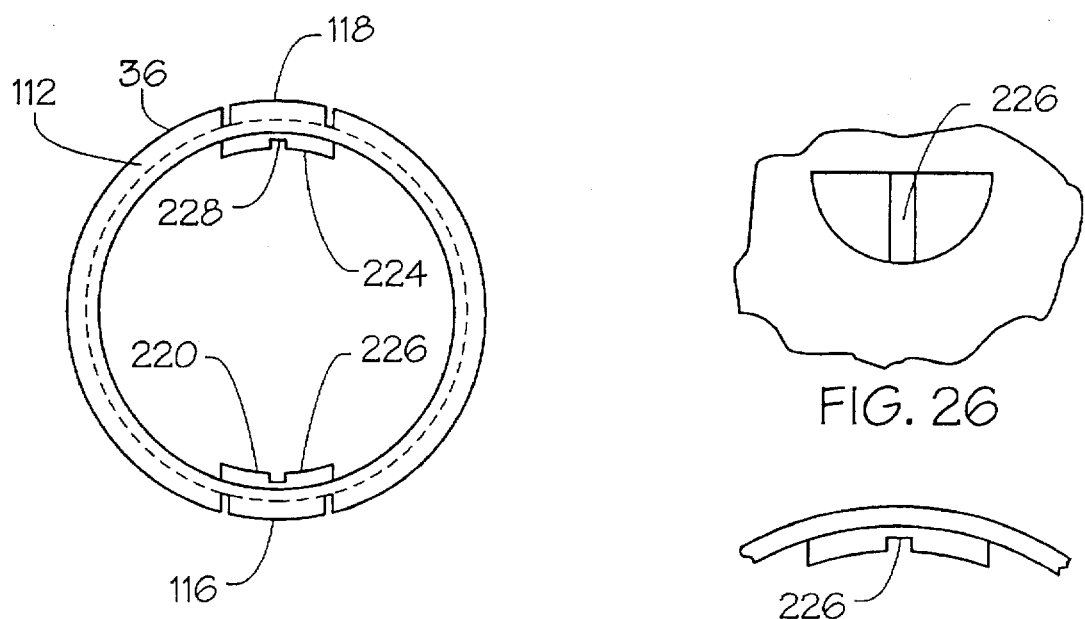
FIG. 25
FIG. 26
FIG. 27

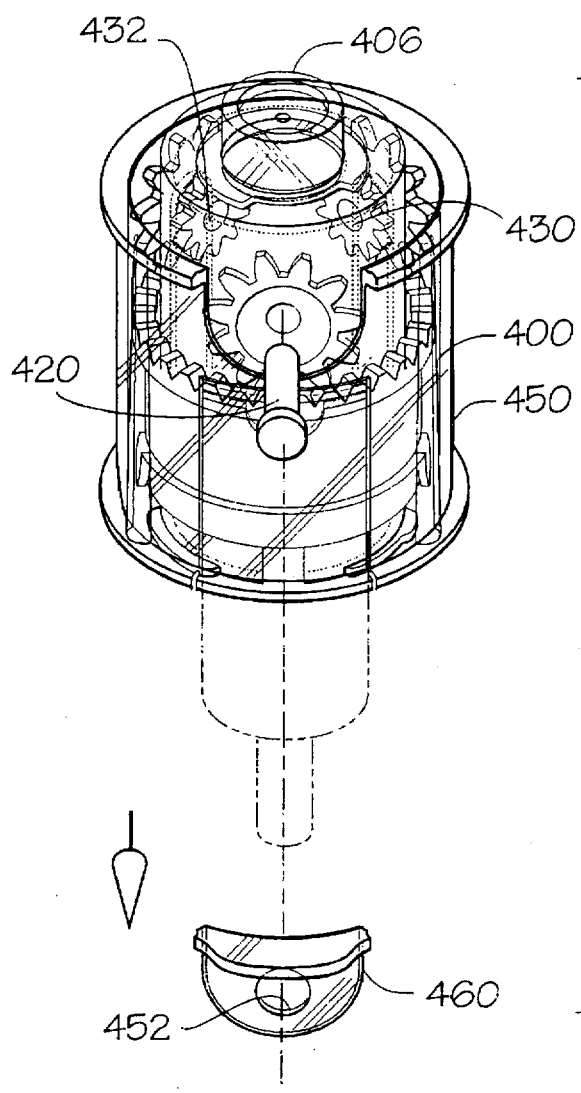
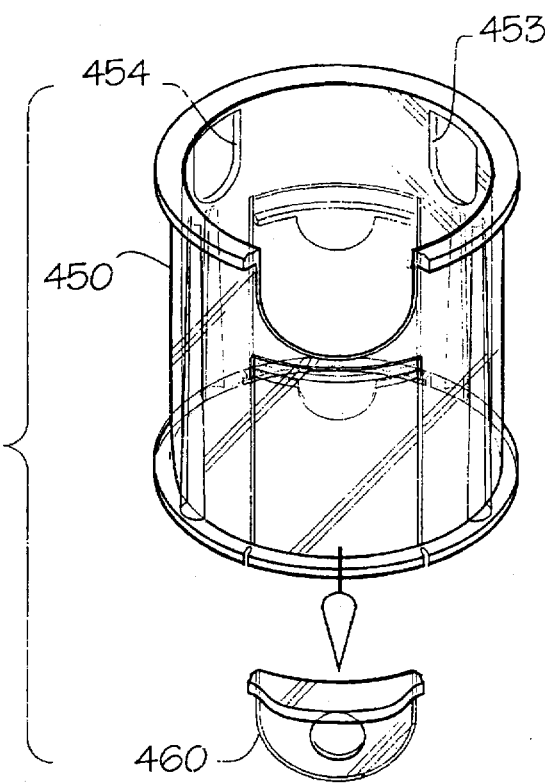
FIG. 39
FIG. 40

KEYLESS CHUCK OPERATION DEVICE

CROSS REFERENCE TO RELATED APPLICATION

This is a continuation-in-part of applicant's U.S. patent application Ser. No. 08/229,437 filed Apr. 12, 1994, now abandoned.

BACKGROUND OF THE INVENTION

This invention relates generally to apparatus and methods for opening and closing the jaws of a chuck of the type used on electric and pneumatic drills and the like. This invention relates particularly to apparatus for providing keyless operation of a chuck head. Still more particularly, the invention relates to a device that may be added to an existing chuck head, without requiring any modifications thereto, for providing keyless operation.

The prior art is replete with unsuccessful attempts to provide satisfactory keyless operation of a chuck head. Keyless operation is desirable for several reasons. An obvious reason is that keyless operation obviates the need for looking for the chuck key. Keyless operation also is faster than using an ordinary chuck key. Often when a drill is in use, the chuck jaws become loose, making it necessary to tighten them before proceeding with further use of the drill. Keyless operation greatly speeds up use of a drill when it becomes necessary to tighten the chuck jaws or change bits.

Previous attempts to provide keyless chuck operation have several disadvantages. One severe limitation is that most of them are dangerous to the user because they require gripping of a rotating component that is driven by the drill. Even if the user wears a glove, these devices can cause severe hand injuries by separating finger tissue from the fingernails. Another limitation is that the prior art devices are expensive to manufacture because they are such complex mechanisms. Many previous devices cannot be used with an existing drill chuck without requiring modification to the drill chuck.

SUMMARY OF THE INVENTION

This invention has particular utility in medical applications of drills, particularly orthopedic surgery. It is necessary to drill a suitable hole before a bone screw can be inserted in a bone. The convenient keyless operation of the chuck head allows such procedures to be completed more quickly and safely.

The present invention also provides apparatus that allows the user to guide the drill more precisely than can be done with previous devices. This feature is useful in all drilling operations. The natural tendency of the rotating drill bit to "walk" before penetrating the object to be drilled can therefore be controlled.

The keyless chuck operation device of the present invention is preferably formed of components that may be conveniently and inexpensively injection molded. Assembly is very simple, and the device is attached to the chuck head without any modifications thereto.

The invention comprises apparatus for keyless opening and closing of the jaws of a drill chuck head having at least one radial passage and a circumferential face gear thereon that includes a main body formed generally as a hollow cylinder having an open end sized for insertion of the chuck head into the main body. The present invention also includes an outer shell formed generally as a hollow cylinder and mounted to the main body. A gear drive assembly is mounted to the main body and engaged with the face gear of the chuck. The present invention further includes means for selectively manually engaging the outer shell with the gear drive assembly such that rotating the chuck head opens or closes the jaws of the chuck, depending upon the direction of rotation.

The outer shell has a free wheeling position in which a person may grasp the outer shell and hold it to guide the drill without causing the chuck jaws to tend to open or close.

The apparatus according to the present invention may further include a locking pin formed integrally with the main body for locking the main body to the chuck head. The locking pin preferably is mounted on a deformable portion of the main body.

Apparatus according to the present invention for keyless opening and closing of the jaws of a drill chuck head having at least one radial passage and a circumferential face gear, may comprise a main body formed generally as a hollow cylinder having an open end sized to have the chuck head placed inside the cylinder. The invention preferably includes at least one cluster gear assembly rotatably mounted to the main body. The cluster gear assembly preferably has an inner bevel gear arranged to be engaged with the face gear of the chuck head. The cluster gear assembly preferably also has an outer gear. The invention preferably includes and a face gear assembly rotatably mounted to the main body. The face gear assembly includes a hollow, generally cylindrical gear body formed for receiving the main body therein and a face gear arranged to be retained in engagement with the outer gear of the cluster gear assembly.

The present invention preferably includes an outer shell formed generally as a hollow cylinder and mounted to the face gear assembly so that the main body, the face gear assembly, the outer shell and the chuck head are essentially concentric. A cam follower preferably is connected to an inner surface of the outer shell, and a cam is formed in the face gear assembly for selective engagement with the cam follower. The outer shell is movable along a longitudinal axis between a first position where the cam follower engages the cam such that rotating the chuck head opens or closes the jaws of the chuck, depending upon the direction of rotation, and a second position where the chuck head, the main body and the face gear assembly rotate freely within the outer shell. The present invention preferably further includes means for preventing the cam follower from becoming inadvertently engaged with the cam.

At least one pin extend radially through the side wall of the main body into a corresponding radial passage in the chuck head to lock the main body on the chuck. The present invention may have three pins angularly spaced apart by about 120° and extending radially through the side wall of the main body into radial passages in the chuck head.

The main body may includes at least one longitudinally aligned slot therein with the cluster gear assembly being mounted in the slot. A neck connects the outer gear and the inner gear together along their longitudinal axes. The neck preferably has a longitudinal passage extending therethrough. A locking pin extends through the longitudinal passage into the radial passage in the chuck head to lock the cluster gear to the main body.

An appreciation of the objectives of the present invention and a more complete understanding of its structure and method of operation may be had by studying the following description of the preferred embodiment and by referring to the accompanying drawings. It is to be understood that the drawings are not to any scale. The size and orientation of the components shown in the drawings are intended to illustrate the important structural features of the invention and are not intended to be engineering drawings suitable for use as blue prints or construction drawings.

BRIEF DESCRIPTION OF THE DRAWINGS

FIG. 15 illustrates engagement of one of the cluster gear assemblies of FIG. 4 with the face gear of FIG. 9;

FIG. 24 is a partial cross sectional view illustrating outer gears in a plurality of cluster gear assemblies engaged with the face gear of FIGS. 9–12 and inner gears in the plurality of cluster gear assemblies engaged with the face gear of a chuck head;

FIG. 25 is a top plan view of a illustrating a cam follower that may be included in the apparatus of FIG. 16;

FIG. 26 is an end elevation view of the apparatus of FIG. 25;

FIG. 27 is a front elevation view of the apparatus of FIG. 26;

FIG. 39 is a perspective view of the apparatus of FIGS. 37 and 38 illustrating a portion of the outer shell having been broken off to remove the keyless chuck operation device from the chuck head;

FIG. 40 is a perspective view showing the outer shell and the broken off portion;

DESCRIPTION OF THE PREFERRED EMBODIMENT

Basic Structure and Method of Operation

Figure 1:
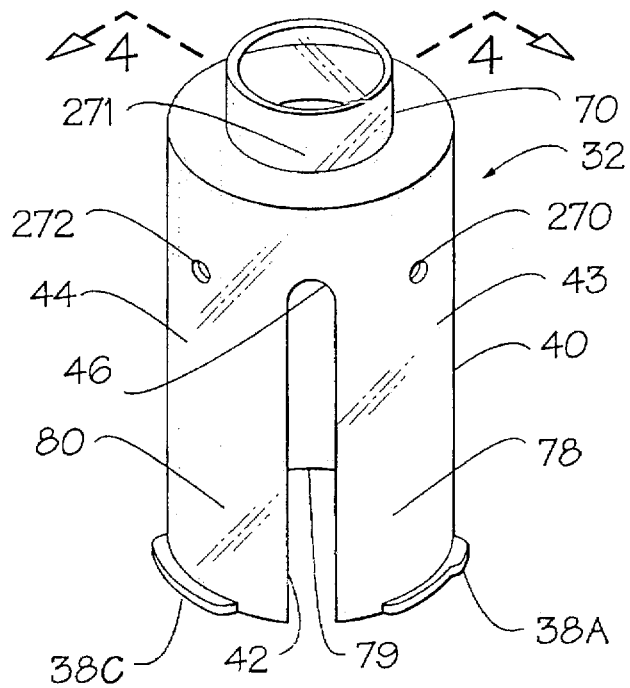
FIG. 1 is a perspective view of a main body of a keyless chuck operation device according to the present invention.
Figure 5:
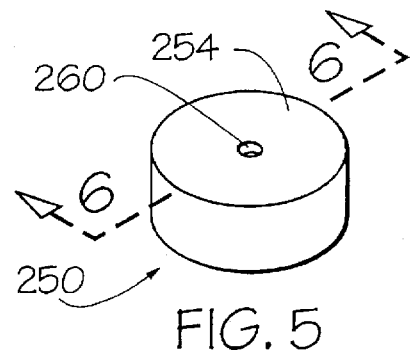
FIG. 5 is a perspective view of an end cap that may be mounted on an end of the apparatus of FIG. 1.
Figure 6:
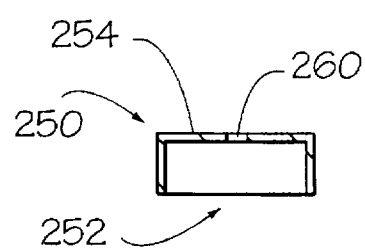
FIG. 6 is a cross-sectional view taken along line 6—6 of FIG. 5.
Figure 2:
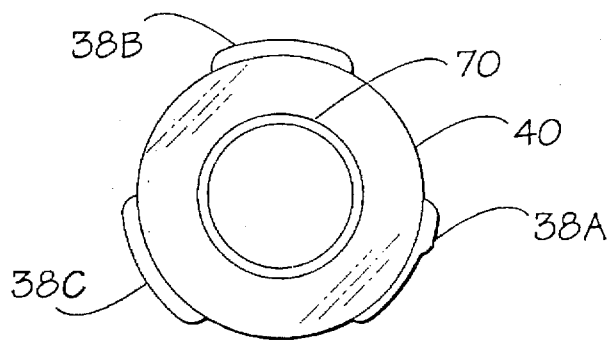
FIG. 2 is a top plan view of the apparatus shown in FIG. 1.
Figure 7:
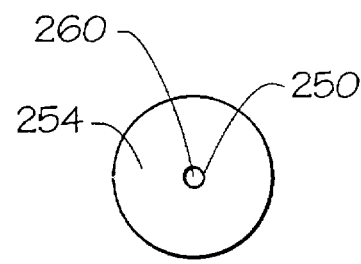
FIG. 7 is a top plan view of the apparatus of FIG. 5.
Figure 3:
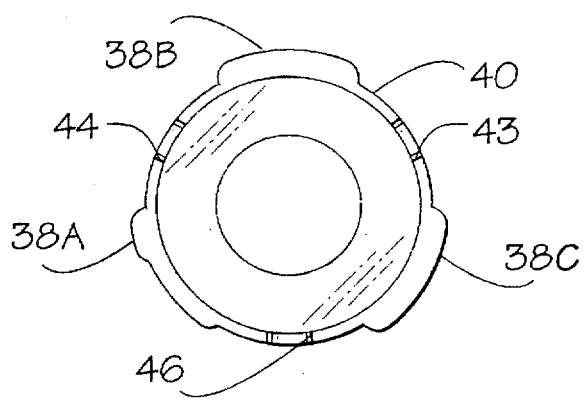
FIG. 3 is a bottom plan view of the apparatus shown in FIG. 1.
Figure 8:
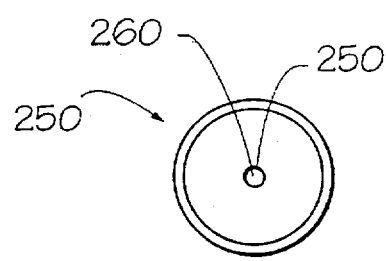
FIG. 8 is a bottom plan view of the apparatus of FIG. 5.

Referring to FIGS. 29–32 a keyless chuck operation device 30 according to the invention includes four main components: (1) a main body 32, (2) a face gear assembly 34, (3) an outer shell 36 and a cluster gear assembly that includes a plurality of cluster gears 50, 62 and 64. The keyless chuck operation device 30 is designed to fit on an existing drill chuck head 31 to provide keyless operation without requiring any modification to the drill or chuck head 31. A plurality of locking pins 200 extend through holes in the cluster gears 50, 62 and 64 to engage the walls of corresponding holes in the chuck head 31 to mount the keyless chuck operation device 30 to the chuck head 31. As described in detail subsequently herein, when the keyless chuck operation device 30 is mounted on the drill chuck head 31, the outer shell 36 may be manipulated to selectively engage or disengage the cluster gears 50, 62 and 64 with a face gear 31 in the drill chuck head 31. When the cluster gears 50, 62 and 64 are engaged with the face gear 31A, applying power to the drill while a user grasps the outer shell and pulls it toward the rear of the chuck head 31 causes the chuck head 31 to rotate inside the keyless chuck operation device 30. This rotation of the chuck head 31 with the cluster gears 50, 62 and 64 engaged with the face gear 31A while the outer shell 36 is held stationary relative to the drill body (not shown) opens or closes the jaws of the chuck head 31, depending upon the direction of rotation. When the face gears 50, 62 and 64 are disengaged from the face gear 31A, the outer shell may be held by one hand of a person using the drill to guide and stabilize the chuck head when the drill is in use.

An advantage of the keyless chuck operation device 30 according to the invention is that it may be added to an existing drill chuck head without any modification thereto. The keyless chuck operation device 30 according to the present invention may also be included in a new drill (not shown) as an original feature. All components of the keyless chuck operation device 30 are preferably made of plastic or other materials that can be manufactured by injection molding processes. The main body 32 and outer shell 36 may be conveniently formed from transparent materials.

Detailed Description of Components and Assembly of the Keyless Chuck Operation Device 30

Because the advantageous functional features of the invention arise from the structures of the components and the methods of assembly of the keyless chuck operation device 30, the various components included in the keyless chuck operation device 30 are described in detail.

Referring to FIGS. 1–4, 29 and 32, the main body 32 may be formed generally as a stepped hollow cylinder having a ranged lower end that includes flange segments 38A, 38B and 38C. The larger diameter portion 40 of the main body 32 includes a plurality of elongated slots 42–44 therein. The slots 42–44 preferably are parallel and spaced 120° apart around the circumference of the larger diameter portion 40.

Figure 4:
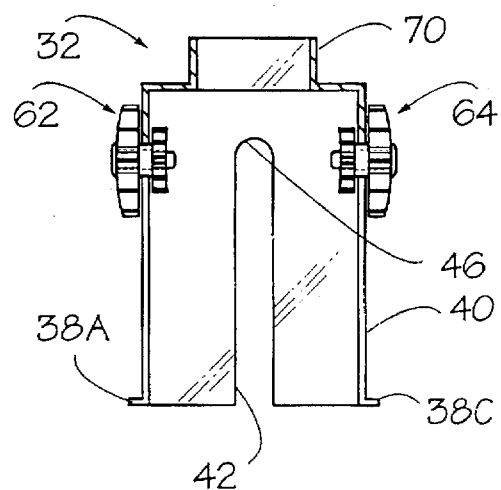
FIG. 4 is a cross-sectional view of the apparatus shown in FIG. 1 with cluster gear assemblies inserted into a pair of slots formed in the main body.
Figure 9:
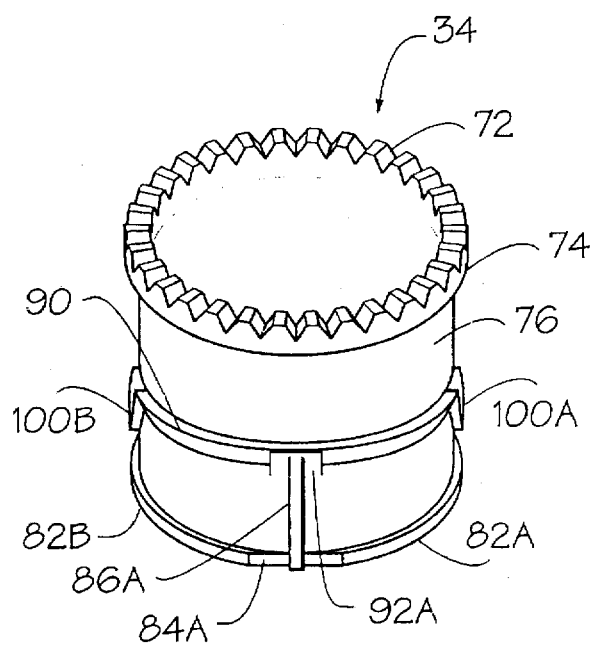
FIG. 9 is a perspective view of a face gear assembly that may be included in the present invention.

The three slots 42–44 are formed to be substantially identical. Therefore, any feature that is described with reference to any one of the slots 42–44 applies also to the other two slots. Referring to FIGS. 1 and 4, the slot 42 has a generally semicircular upper end 46. The diameter of the semicircular upper end 46 is preferably slightly larger than the width of the slot 42.

Referring to FIGS. 12, 22–24 and 28 a cluster gear assembly 50 is mounted in the slot 42 and placed in the semicircular upper end 46. The cluster gear assembly 50 includes an outer cluster gear 51A and an inner cluster gear 51B that are joined by a cylindrical shoulder 56. The cylindrical shoulder 56 of the cluster gear assembly 50 fits within the slot 42 so that the shaft rotates while in contact with the rounded upper end 46.

The keyless chuck operation device 30 should have dimensions appropriate for the specific chuck for which it is designed to be used. The type of keyless chuck operation device 30 described herein is particularly useful with drill chucks used in orthopedic surgery. However it has been found that for this type of chuck there is a lack of uniformity in the positioning of the holes in the inner chuck cylinder 31A. Therefore, the shoulder 56 has a small range of movement in the semicircular upper end 46 of the slot 42. The width of the slot 42 preferably is about the same as the diameter of the shoulder potion 56 of the cluster gear assembly 50. The diameter of the upper end is slightly larger than the diameter of the shoulder portion 56, which allows a small amount of lateral movement of the cluster gear relative to the main body 32 when the cluster gear assembly 509 is mounted in the upper end 46 of the slot 42. This lateral movement of the cluster gear 50 relative to the main body 32 allows adjustment of the exact location of the cluster gear assembly 50 to be adapted to fit chucks that have small variations in the locations of the holes in the chuck inner cylinder 31A.

The outer surface 58 of the outer cluster gear 51A may be convexly curved so that it will conveniently fit within a cylinder as described subsequently. The inner cluster gear 51B has an inward facing surface 60 that may be curved to facilitate inserting a cylinder inside the main body 32.

Cluster gear assemblies 62 and 64 are mounted in the slots 43 and 44 in the same manner as the cluster gear assembly 50 is mounted in the slot 42. The cluster gear assembly 62 includes an outer gear 63A and an inner gear 63B, and the cluster gear assembly 64 includes an outer gear 65A and an inner gear 65B. The three cluster gear assemblies all have substantially identical forms and functions. The main body 32 preferably is formed of a transparent plastic material, which facilitates aligning the slots 43, 44 and 46 with the holes in the chuck head 31.

The main body 32 may include a smaller diameter upper portion 70 that is formed as a hollow cylinder. When the keyless chuck operation device 30 is mounted to the chuck head 31, the jaws of the chuck head 31 extend into the upper portion 70 when the chuck jaws are closed. The smaller diameter portion 70 allows the upper end of the main body to have a small diameter opening 71, which aids in preventing entry of contaminants into the keyless chuck operation device 30.

Figure 11:
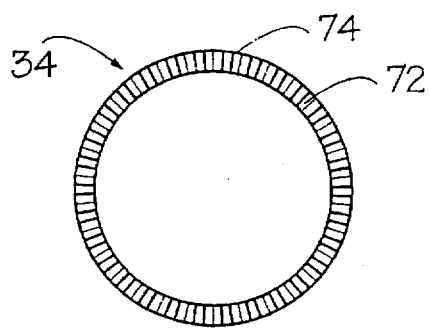
FIG. 11 is a top plan view of the apparatus of FIG. 9.
Figure 12:
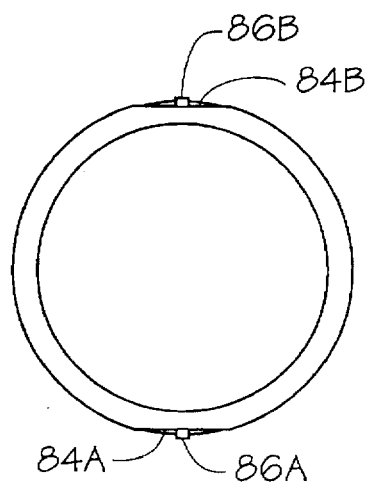
FIG. 12 is a bottom plan view of the apparatus of FIG. 9.

Referring to FIGS. 9–13, the face gear assembly 34 includes a face gear 72 formed on a flanged end 74 of a generally cylindrical gear body 76. The gear body 76 has an inner diameter that is slightly larger than the outer diameter of the main body 32, but less than the outer diameter of the flange segments 38A, 38B and 38C. The portions 78–80 of the main body 32 between the slots 42–44 are sufficiently flexible that the flanges 38A, 38B, 38C may be manually deflected radially inward so that the inner diameter of the cylindrical gear body 76 is greater than the outer diameter of the lower end of the main body 32. Referring to FIG. 12, the cylindrical gear body 76 is then slid over the flanges 38A, 38B, 38C to mount the cylindrical gear body 76 on the main body 32. The flanges 38A, 38B, 38C are then released and allowed to resume their normal configurations. The gear body 76 is then retained between the flanges 38A, 38B, 38C and the cluster gear assemblies 50, 62 and 64.

As shown in FIGS. 12, 15, and 21–23, when the face gear assembly 34 is mounted on the main body 32, the outer cluster gear 62 engages the face gear 72. The face gear assembly 34 is rotatable on the main body 32. Rotation of the face gear assembly 34 relative to the main body 32 causes the outer cluster gears 51A, 63A and 65A to rotate. The inner cluster gears 51B, 63B and 65B are rigidly connected to the corresponding outer cluster gears 51A, 63A and 65A, respectively. Therefore, the rotating outer cluster gears 51A, 63A and 65A causes the inner cluster gears 51B, 63B and 65B to rotate at the same angular rate.

The cylindrical gear body 76 has end flanges 82A and 82B that extend around most of the circumference of the lower end 84 of the cylindrical gear body 76. When the gear body 76 is mounted on the main body 32, the end flanges 82 and 82B engage the end flanges 38A, 38B, 38C so that the gear body 76 is retained on the outer surface of the main body 32. Between the flanges 82A and 82B there are flattened portions 84A and 84B. Near the center of the flattened portions 84A and 84B there are raised generally rectangular keyways 86A and 86B. The keyways 84A and 84B are arranged 180° apart on the outer surface of the gear body 76.

Referring to FIGS. 9, 10, 12 and 13, near the center of the length of the gear body 76 there is a flange 90 that extends around the gear body 76. The keyways 86A and 86B intersect the flange 90. The distance between the flange 90 and the lower end of the gear body 76 is greater at the keyways 86A and 86B than at other locations around the circumference of the gear body 76. Near the intersection of the keyways 86A and 86B with the flange 90 there are a pair of small wedges or cams 92A and 92B, respectively. Approximately 90° from the keyways 86A and 86B there are a pair of cams 100A and 100B in the flange 90.

Figure 10:
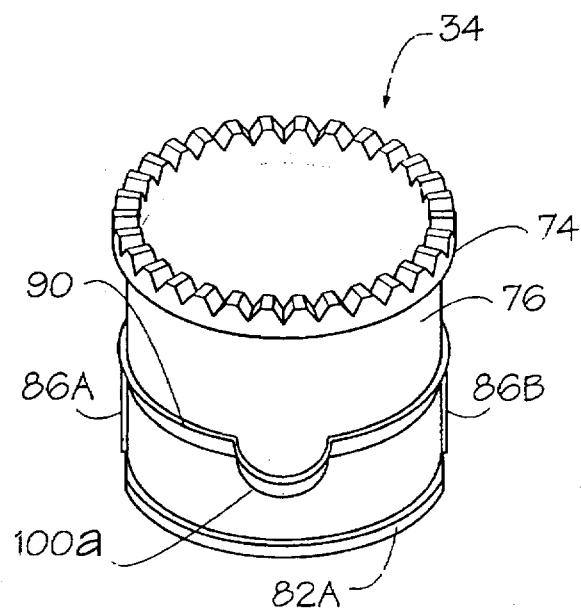
FIG. 10 is a perspective view of the face gear assembly of FIG. 9 rotated 90°.
Figure 13:
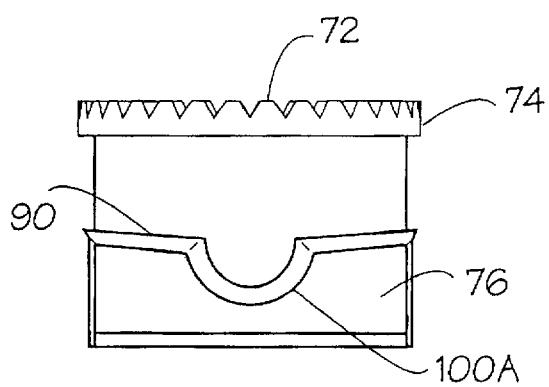
FIG. 13 is a front elevation view of the apparatus of FIG. 10.
Figure 14:
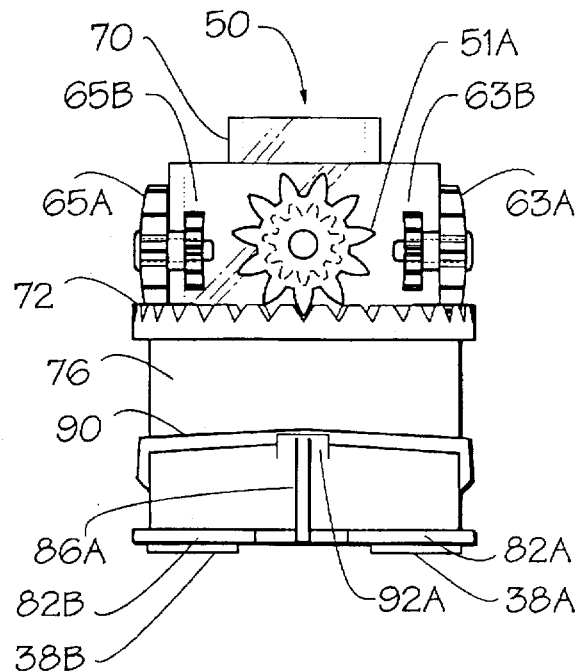
FIG. 14 is a front elevation view of the apparatus of FIG. 9 mounted on the main body of FIGS. 1–4.

Referring to FIGS. 10 and 11, the face gear assembly 34 may include a ring 93 around the face gear 72. The ring 93 retains lubricant (not shown) in the face gear 72 while it is rotating. Without the ring 93 there is a tendency for lubricant to move radially out of the gear 72 as it rotates with the chuck head.

Figure 16:
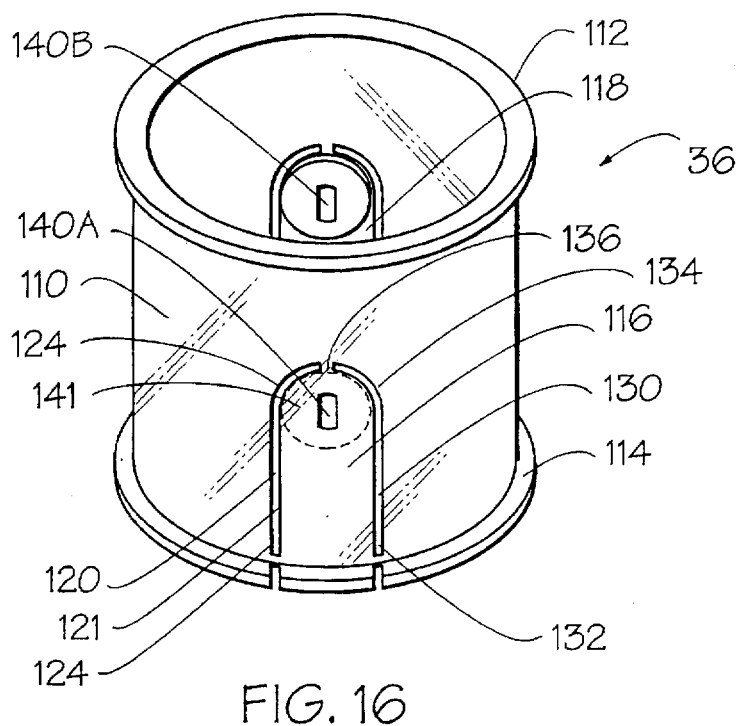
FIG. 16 is a perspective view of an outer shell of the keyless chuck operation device according to the present invention.
Figure 21:
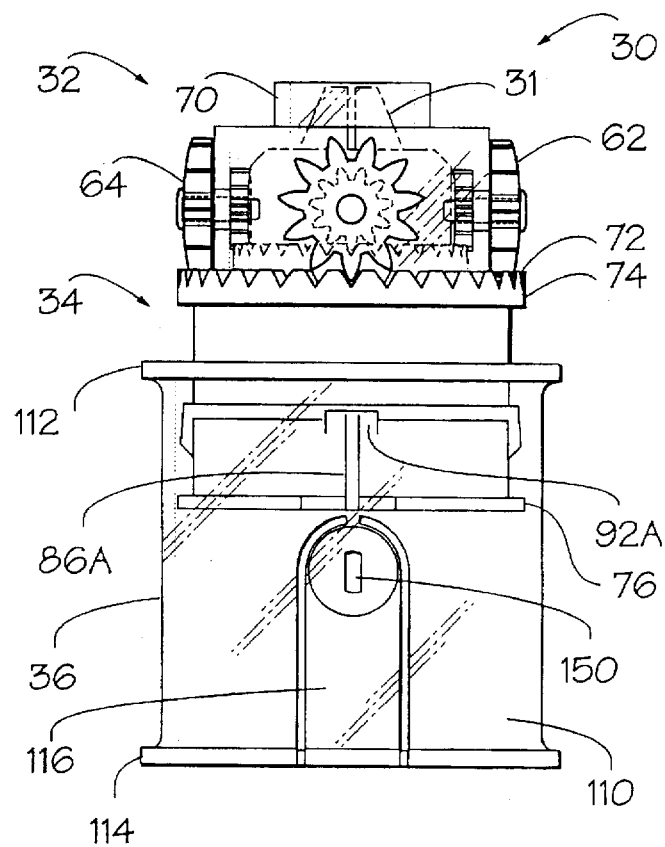
FIG. 21 illustrates the face gear assembly mounted to the main body and the outer shell being installed on outer shell.
Figure 17:
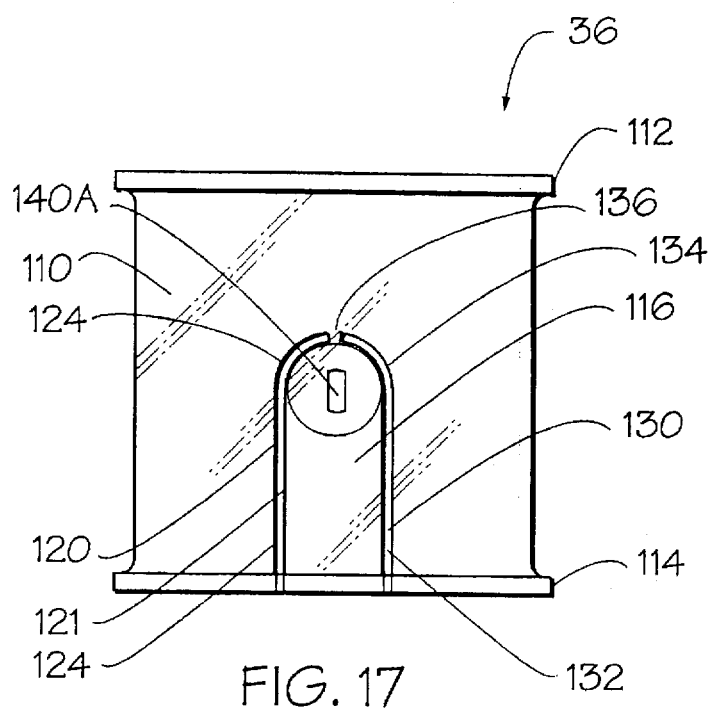
FIG. 17 is an elevation view of the apparatus of FIG. 16.
Figure 22:
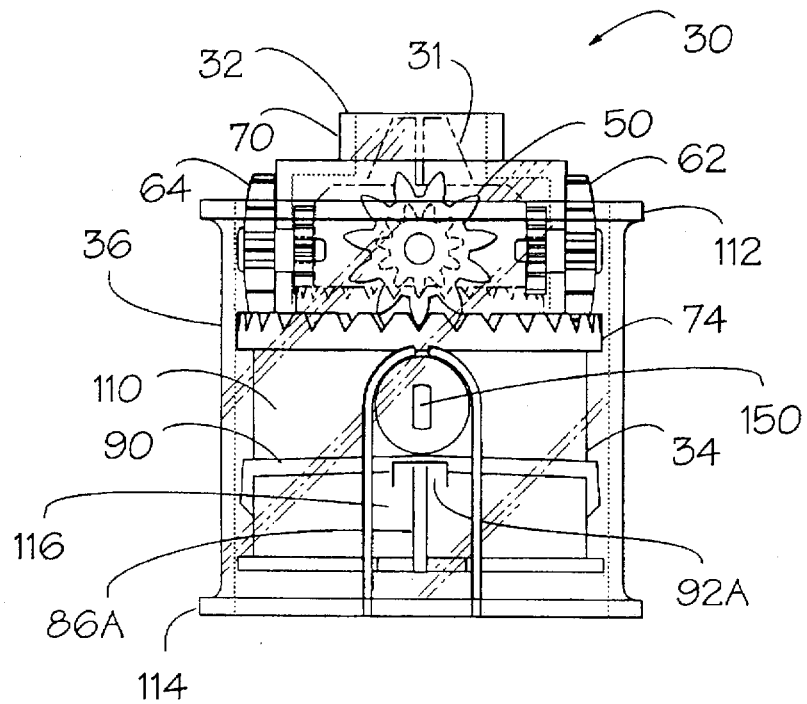
FIG. 22 illustrates the outer shell of FIG. 16 in a free-wheeling position on the face gear assembly of FIG. 9.
Figure 23:
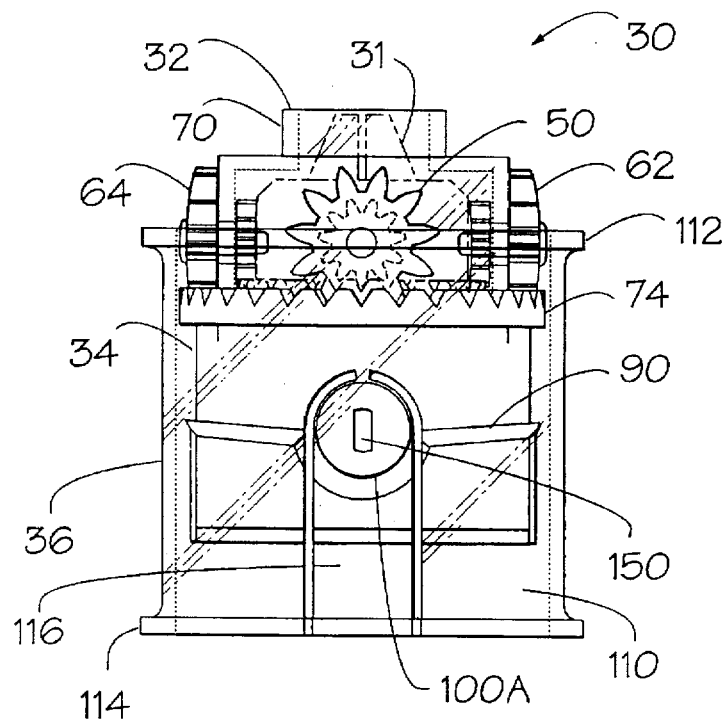
FIG. 23 illustrates the outer shell of FIG. 16 in a rearward position where the cam followers in the outer shell engage locking cams in the face gear assembly.
Figure 29:
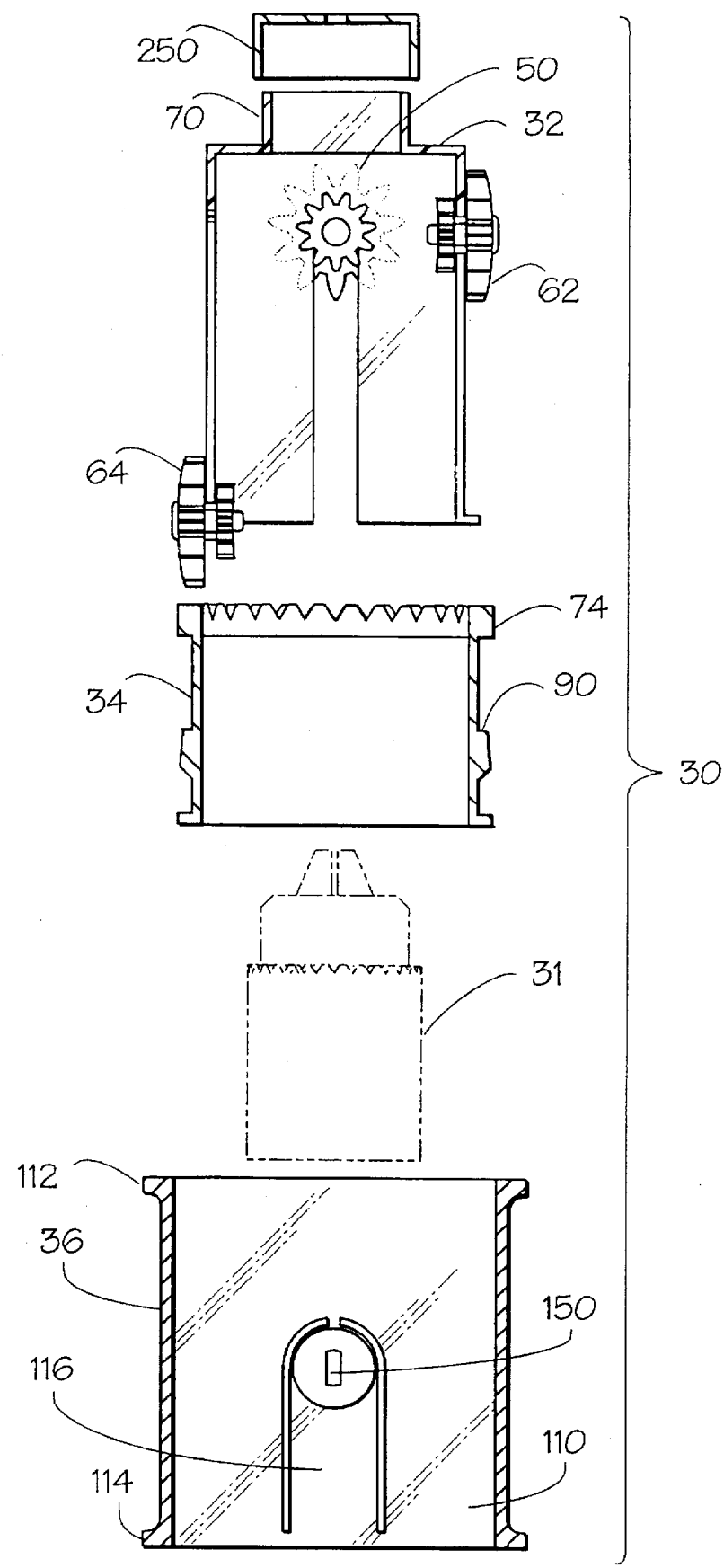
FIG. 29 is an exploded cross sectional view of a keyless chuck operation device according to the invention.
Figure 30:
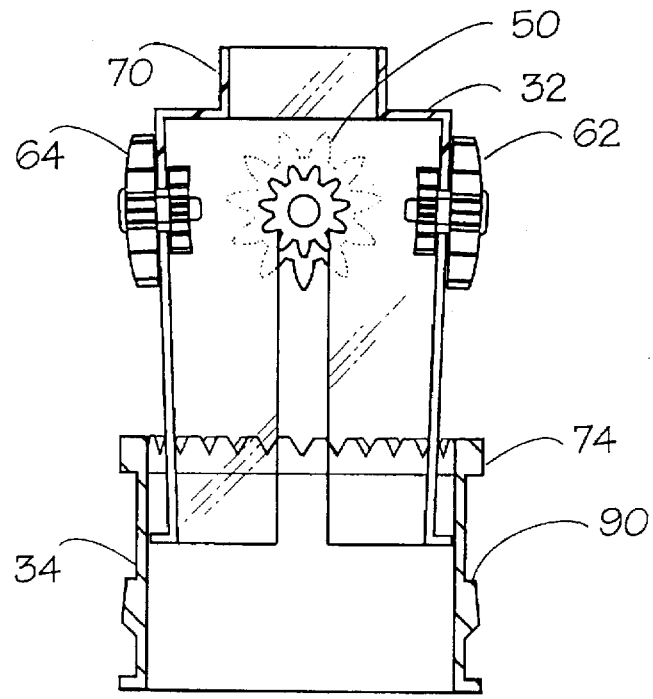
FIG. 30 is a cross sectional view illustrating the face gear and the cluster gears mounted to the main body of the keyless chuck operation device of FIG. 29.
Figure 31:
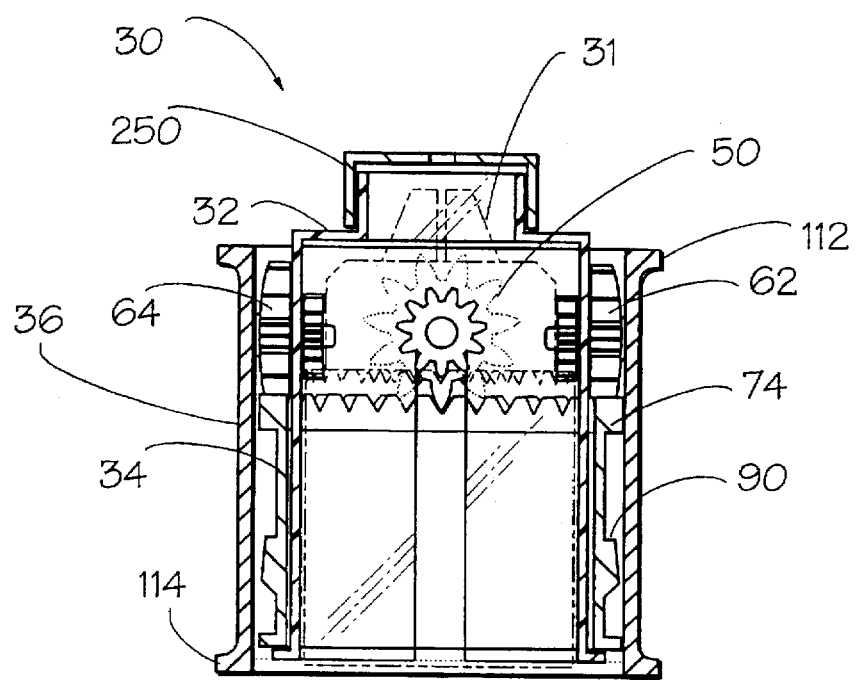
FIG. 31 is a cross sectional view showing the fully assembled keyless chuck operation device mounted to a drill chuck head.
Figure 32:
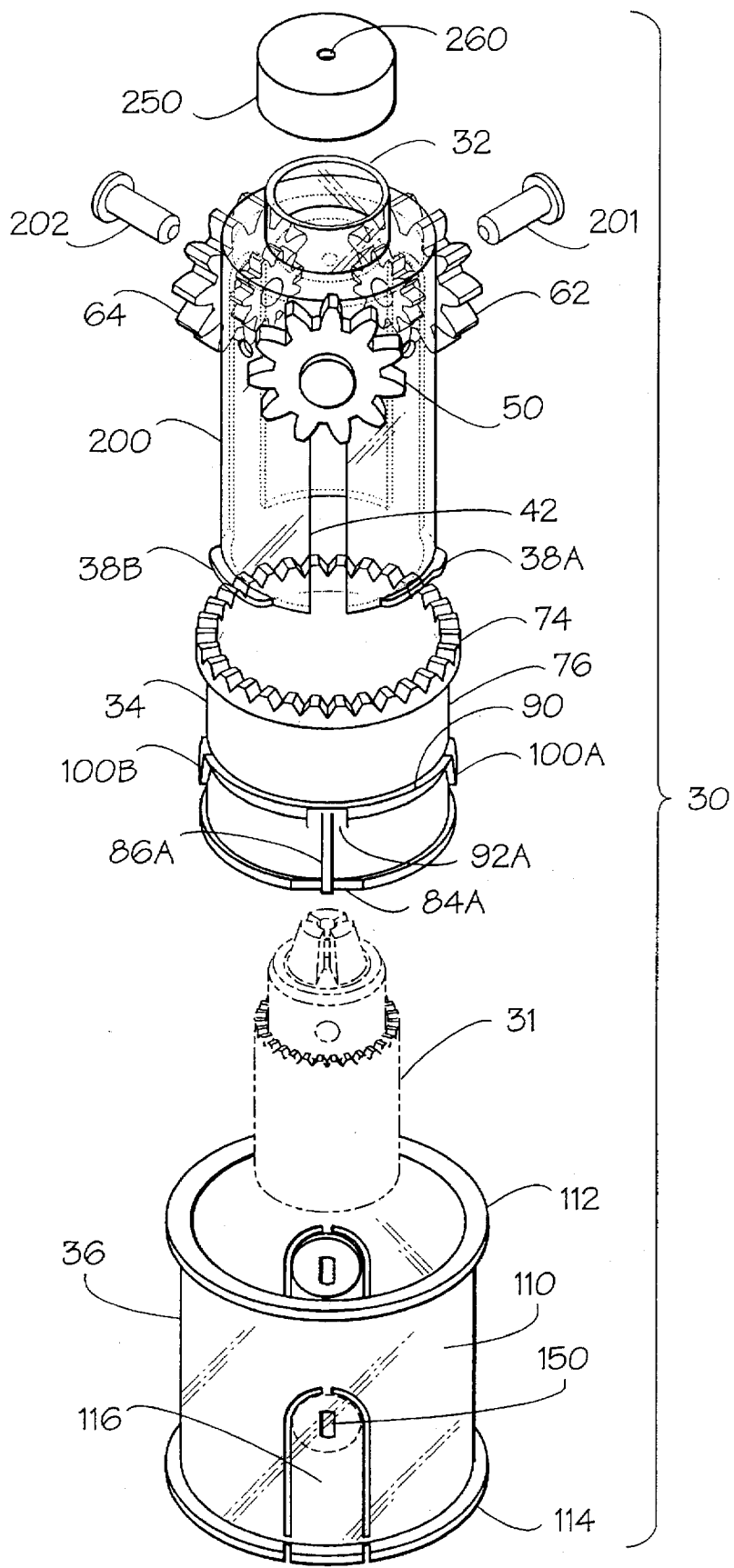
FIG. 32 is an exploded perspective view of the apparatus of FIG. 32 showing the keyless chuck operation device and the drill chuck head.

Referring to FIGS. 16–17, the outer shell 36 is formed to have a generally hollow cylindrical body 110. The outer shell 36 has an upper flange 112 and a lower flange 114. The outer shell 36 is open at both ends to permit it to be slidable upon the gear body 76. The cylindrical body 110 has a first flexible portion 116 and a second flexible portion 118 that allow the outer shell to be slid over the gear body 76.

The first and second flexible portions 116 and 118 are substantially identical. Therefore, only the first flexible portion 116 is described in detail herein. Referring to FIGS. 16 and 17, an elongate slot 120 is formed in the cylindrical body 110. The slot 120 has a main portion 121 that is parallel to the longitudinal axis of the cylindrical body 110. Between the lower end 122 and upper end 124 of the slot 120, the slot extends completely through the sidewall of the cylindrical body. The slot 120 preferably extends through a portion of the bottom flange 114. The slot 120 preferably does not extend completely through the cylindrical body 110 in the region adjacent the flange 114. The upper end 124 of the slot 120 preferably is formed as an arc of a circle.

A second slot 130 is formed in the cylindrical body 120. The slot 130 has a main portion 132 that is substantially identical to the main portion 121 of the slot 120. The slot 130 has an upper portion 134 that is symmetrical with upper end 124 of the slot 120. A portion 136 of the sidewall of the cylindrical body 110 lies between the upper ends 124 and 134 of the slots 120 and 130, respectively. Therefore, the flexible portion 116 of the cylindrical body is connected to the cylindrical body 110 at the flange 114 and at the upper end 136 of the flexible portion.

Figure 18:
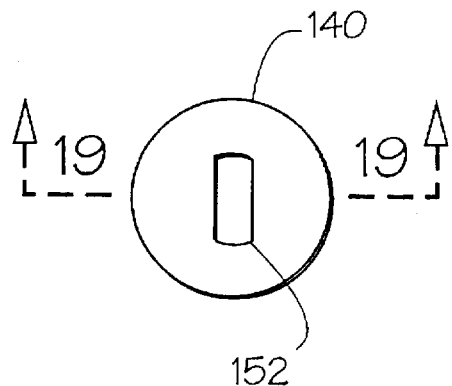
FIG. 18 is a top plan view of a cam follower that may be used to mount the outer shell of FIG. 16 to the face gear assembly of FIGS. 9–12.
Figure 20:
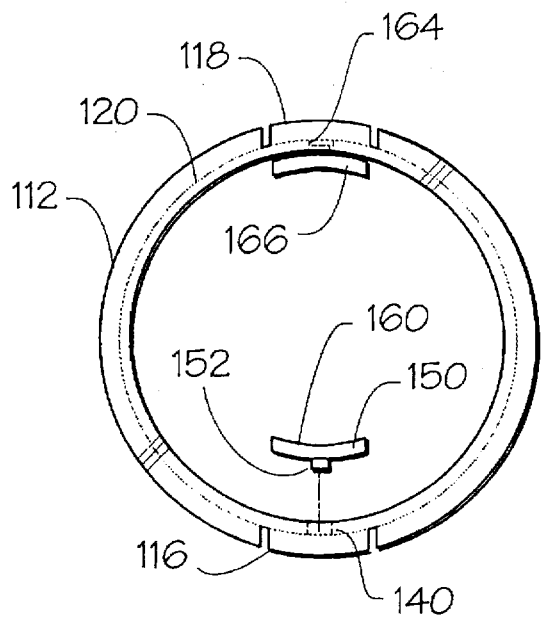
FIG. 20 is a top plan view of the outer shell of FIG. 16 with cam followers according to FIGS. 18 and 19 installed in holes in the outer shell.
Figure 19:
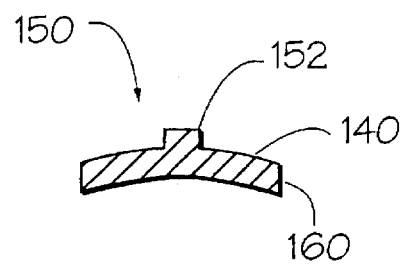
FIG. 19 is a cross-sectional view of the cam follower taken along line 19—19 of FIG. 18.

A small passage 140A is formed in the flexible portion 116 near its upper end 141. Referring to FIGS. 18, 19 and 20, a cam follower 150 may be mounted in the passage 140. It is to be understood that the drawings are not to any particular scale. The various components are illustrated in sizes that are convenient for showing their essential features. The cam follower 150 has a mounting rod 152 that extends into the passage 140. A retainer portion 160 that is preferably formed integrally with the mounting rod 152 extends into the interior of the outer shell 36. The retainer portion 160 has a curved inner surface 162 that has the same curvature as the inside surface of the outer shell 110. The retainer portion 160 has a curved outer surface 164 that has the same curvature as a portion of the gear body 76 between the flanges 74 and 90. The cam followers 150 preferably has a beveled leading edge 165 as shown in FIG. 18B that facilitates mounting the outer shell 26 on the gear body 76.

Referring to FIG. 20, a cam follower 166 may be mounted in a passage 168 in the cylindrical body 120. The cam follower 166 preferably is formed to be identical with the cam follower 150.

The inner diameter of the outer shell is slightly larger than the outer diameter of the gear body 76. To mount the outer shell 36 on the gear body 76, the cam followers 150 and 166 are first mounted to the outer shell 36 as described above. The outer shell 36 is then aligned with the gear body 76 with the lower end of the gear body 76 adjacent the open upper end of the outer shell 36. The angular orientations of the outer shell 36 and the gear body 76 are adjusted so that the cam followers 150 and 166 are aligned with the keyways 86A and 86B. The outer shell 36 is then moved a short distance so that the cam followers 150 and 166 come into contact with the wedges 92A and 92B. This is called the pre-load position and is helpful mounting of the keyless chuck operation device 30 on the chuck head 31.

To mount the keyless chuck operation device 30 on a drill chuck, the gear body 76 is first mounted on the main body 32 as described above. The end of the chuck head 31 is inserted through the outer shell 36, and the assembled main body 32 and gear body 76 until the three holes 182–184 (shown in FIG. 24) in the chuck head line up with the center holes 186–188 in the cluster gear assemblies 50, 62 and 64. Locking pins 200–202 are then inserted through the holes 186–188 in the cluster gear assemblies 50, 62 and 64 into the three holes 182–184 in the chuck head.

The outer shell 36 and the gear body 76 are then pressed toward one another along their longitudinal axes. The cam followers 150 and 166 "ride up" on the keyways 86 and 86B. The beveled leading edges of the cam followers make it easy to slide the outer shell and cam followers over the gear body 76 and the flange 90. As the outer shell is advanced on the gear body 76, the flexible portions 116 and 118 bulge radially outward to allow the outer shell to be mounted on the gear body 76. The cams 92A and 92B aid in slipping the outer shell 110 and cam followers 150 and 166 over the flange 90 in the gear body 76. Once the cam followers 150 and 166 have passed over the flange, the flexible portions 116 and 118 return to their normal positions.

The outer shell 110 is then easily moved longitudinally with respect to the gear body so that the cam followers 150 and 166 move between the flanges 74 and 90. The upper end of the outer body covers the heads of the locking pins, which prevents them from coming out of their respective holes in the cluster gears and the chuck head.

To operate the chuck jaws, the user firmly grasps the outer shell 110 with one hand and hold the drill with his other hand. The outer shell 110 is then urged toward the body of the drill while the chuck trigger is pressed to make the chuck rotate. The cam followers 150 and 166 then move into engagement with the cams 100A and 100B in the flange 90. The cam followers 150 and 166 cooperate with the cams 100A and 100B to exert a torque on the gear body 76 and the face gear 72. This torque is then transmitted through the cluster gear assemblies 50, 62 and 64 to the chuck head. The outer portion of the chuck head is held stationary by the keyless chuck operation device 30 while the inner portion of the chuck head is rotated by the drill motor. The result is that the chuck jaws then either open or close, depending upon whether the drill is set to rotate in the forward direction or the reverse direction.

When the outer shell is in its neutral position, a person may grasp the outer shell 36 to hold the end of the drill steady and to guide the drill bit to the location where drilling is to be done. A small amount of forward force may be exerted on the outer shell during drilling, which causes the cam followers 150 and 166 to slide against the upper flange 74 of the gear body 76. The slightly raised portions of the flange 90 at the junctions of the flange 90 and the cam followers 86A and 86B bump against the cam followers 150 and 166 as the drill rotates while in use. This bumps the cam followers 150 and 166 away from the cams 100A and 100B and helps prevent inadvertent engagement of the cam followers with the recesses, which would tighten or loosen the chuck jaws. Therefore, the keyless chuck operation device 30 may be used in any orientation without any risk of the cam followers 150 and 162 becoming accidentally engaged in the cams 100A and 100B.

In designing the gears, it should be noted that a standard drill chuck as used in orthopedic applications has a face gear on the outer cylinder 31B that has thirty-one gear teeth. In the preferred embodiment of the invention the inner cluster gears 51B, 63B and 65B each have eleven teeth, and the outer cluster gears 51A, 63A and 65A also each have eleven teeth. The face gear 72 should have the same number of teeth as the face gear on the chuck head. It is essential that the cluster gear assemblies 50, 62 and 64 and the face gear cooperate with the face gear on the chuck head so that the face gear 72 and the face gear on the chuck head rotate through the same angle as when the cam followers 150 and 166 of the outer shell 36 are engaged with the cams 100a and 100B, respectively of the gear body 76.

Referring to FIGS. 25–27, the outer shell 36 may have cam followers 220 and 224 formed integrally with the flexible portions 116 and 118. The cam follower 220 preferably includes a slot 226 that is aligned lengthwise with the keyway 86A. The cam follower 224 preferably includes a slot 228 that is aligned lengthwise with the keyway 86B. To mount the outer shell 26 on the gear body 76, the slots 226 and 228 are aligned with the keyways 86A and 86B, respectively. The outer shell is the pressed onto the gear body 76 so that the keyways 86A and 86B pass through the slots 226 and 228.

Referring to FIGS. 5–8, the keyless chuck operation device 30 may include a cap 250 that may be mounted on the upper end 70 of the main body 32 of FIG. 1. The upper portion 70 of the main body 32 may include a circumferential boss 251 spaced a short distance from the opening 71.

The cap 250 preferably is formed as a thin-walled cylinder having an open end 252 and a closed end 254. The cap 250 includes a central passage 260 in the closed end 254. When the cap is mounted on the main body 30, the passage 260 is aligned with the center of the drill chuck. The closed end 254 is preferably flexible so that drill bits (not shown) of various diameter may be inserted through the passage 260 into the open chuck. The edge of the passage 250 closes around the bit, which aids in preventing material from entering the keyless chuck operation device 30.

Referring to FIG. 1, the locking pins 200–202 may be inserted through holes 270–272 in the main body 32 instead of through the holes in the cluster gear assemblies 50, 62, 64. When the locking pins 200–202 are inserted through the cluster gears, the holes through the gears must be approximately the same diameter as the diameter of the holes in the chuck head. If the locking pins 200–202 are inserted through holes in the main body, the holes in the cluster gear assemblies may be made larger, which reduces the amount of material required to form them.

Figure 28:
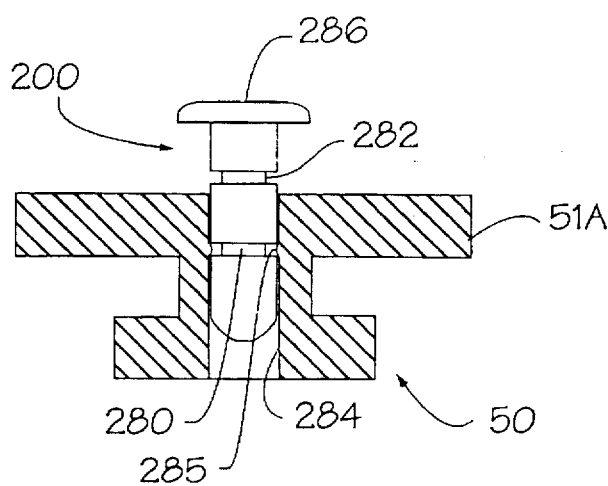
FIG. 28 illustrates a two stage locking pin that may be used to mount the keyless chuck operation device according to the present invention to a drill chuck head.

Referring to FIG. 28, the locking pin 200 may be formed to have two circumferential locking grooves 280 and 282.

The pointed end 283 of the pin is inserted into the hole 284 in the cluster gear assembly 50, for example. The cluster gear assembly 50 includes a circumferential boss 285 inside the hole 284. The first locking groove 280 and the boss 285 are engaged to retain the pin 200 in the hole 284 in the preload position. The pin 200 will not fall out of the hole 284 and will not slip through without exertion of pressure on the pin head 286. This prevents the locking pins from interfering with the insertion of the chuck head into the main body 32. Once the chuck head is inserted and the holes in the chuck head are aligned with the ends of the locking pins 270–272, pressure is exerted on the locking pins to push them into the holes in the chuck head. The second locking stage groove 282 and the boss 285 are then engaged together to prevent the pin 200 form falling out of the gear 50. The locking pins 201 and 202 preferably are formed to be identical to the locking pin 200. Therefore, the pins 201 and 202 are not described in detail herein.

Figure 33:
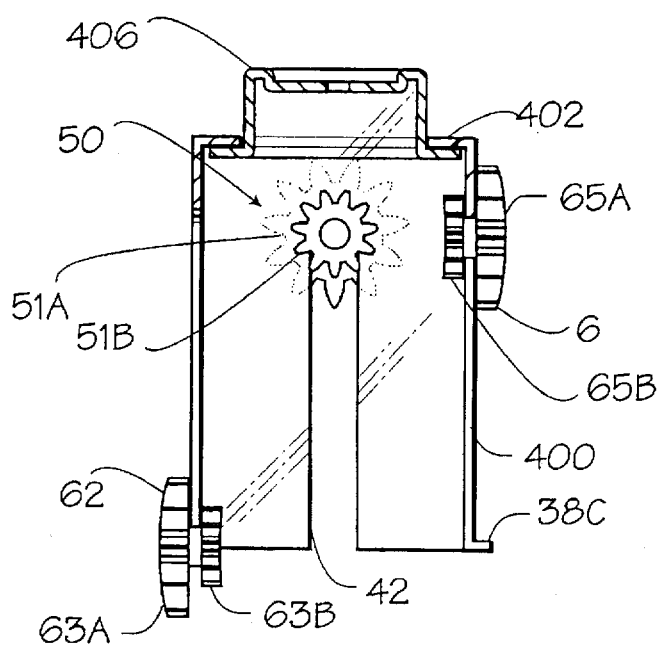
FIG. 33 is a partial cross sectional view illustrating an alternate embodiment of an end cap that may be mounted to the main body.

Referring to FIG. 33, there is shown an alternative structure for the main body and end cap. The main body 400 of FIG. 33 is formed generally as a hollow cylinder having a flanged lower end similar to what is shown in FIG. 1. The main body 400 does not include the reduced diameter portion 70 as shown in FIG. 1. Instead, the main body 400 has a flat upper end wall 402 with a circular passage 404 therein.

FIG. 33 also shows an end cap 406 mounted in the main body 400. The end cap 406 is formed generally as a cylinder having a flange 408 around its lower end as seen in FIG. 33. The end cap 406 is inserted into the main body 400 from the open lower end thereof and positioned so that the end cap 406 protrudes from the circular passage 404 in the main body 400 with the flange 408 engaging the inside of the end wall 402. The end cap may be secured in the opening 404 by friction between the outside of the end cap 406 and the walls of the opening 404. Another means for retaining the end cap in its desired position is friction between the outer edge of the flange 408 and the inner wall of the main body 400. It is also possible to secure the end cap and the main body together by an adhesive placed between the flange 408 and the inside of the end wall 402. The end cap 406 also includes a small diameter passage 410 to allow a drill bit or the like to extend through the end cap 408 to the drill chuck 31 (not shown in FIG. 33). The structure of the main body 400 and the end cap 408 prevents any inadvertent removal of the end cap 408 from its desired position on the main body 400.

Figure 34:
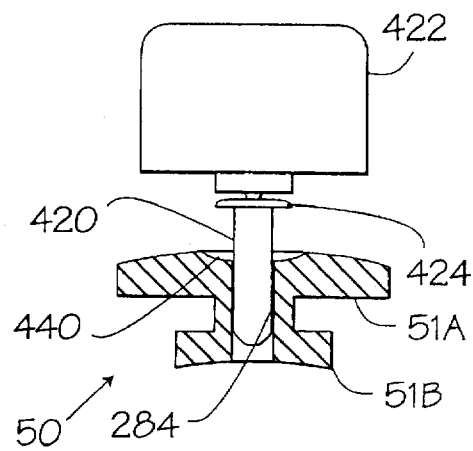
FIG. 34 is a partial cross sectional view showing a locking pin partially inserted into a hole in one of the cluster gears.
Figure 36:
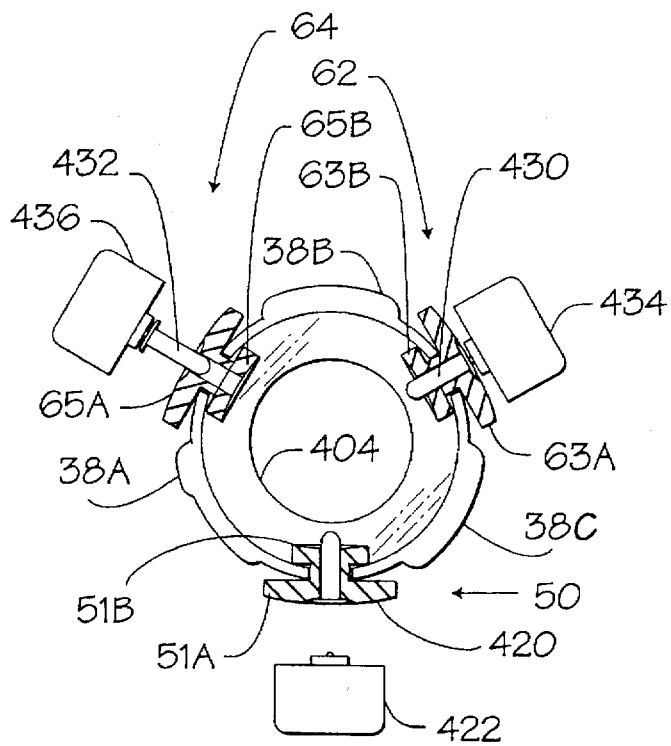
FIG. 36 is a plan view showing three cluster gears mounted to the main body with locking pins partially inserted into holes in the cluster gears as a step in the assembly of the keyless chuck operation device.
Figure 35:
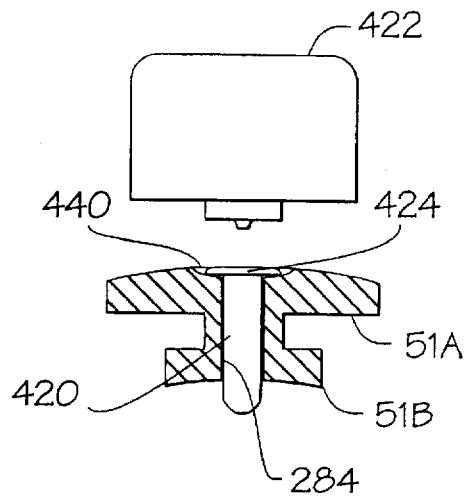
FIG. 35 is a partial cross sectional view showing the locking pin of FIG. 34 fully inserted into the cluster gear with the head of the locking pin having been removed.
Figure 37:
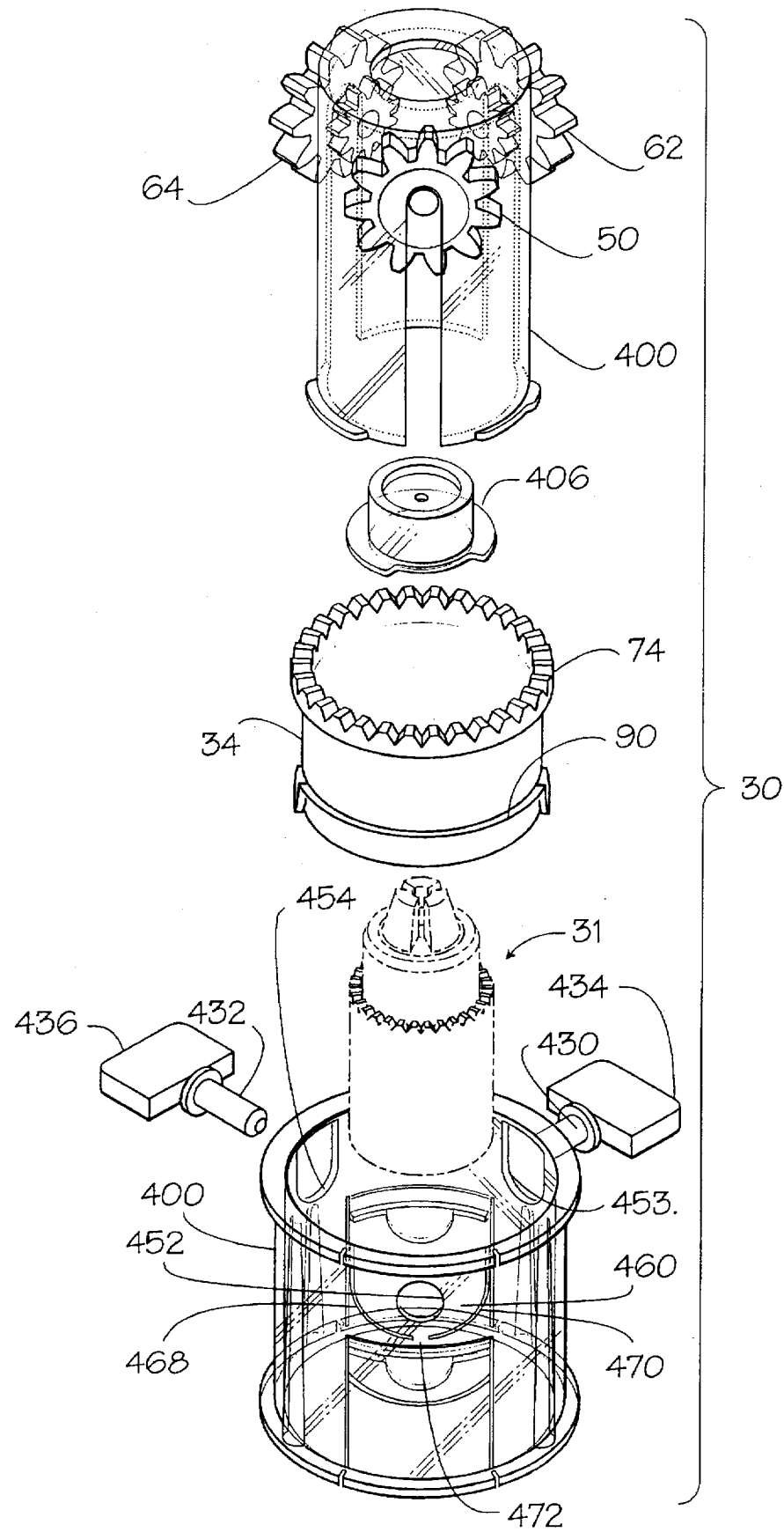
FIG. 37 is an exploded perspective view of an alternate embodiment of a keyless chuck operation device.

FIGS. 34–36 illustrate an alternate mounting pin structure that may be used for mounting the cluster gear assemblies 50, 62 and 64 to the main body 32. As shown in FIGS. 34 and 35, a mounting pin 420 extends into the central passage 284 of the cluster gear assembly 50 in the manner shown in FIG. 28. A tab 422 is connected to the head 424 of the mounting pin 420 by a small-diameter portion of the plastic material used to form the mounting pin 420.

Referring to FIG. 36, mounting pins 430 and 432 are inserted into the cluster gears 62 and 64, respectively, in the manner shown and described for the mounting pin 420 and the cluster gear 50. It should be noted that initially the mounting pins 420, 430 and 432 extend into the cluster gears 50, 62 and 64 only a small distance as shown for the pin 420 of FIG. 1 and the pin 432 of FIG. 36. After the keyless chuck operation device 30 is placed on the chuck head 31, and the locking pins 422, 430 and 432 are properly aligned with the corresponding holes in the chuck head 31, the pins 422, 430 and 432 are fully inserted into the holes in the cluster gears 50, 62 and 64 as shown for the pin 430 in FIG. 36.

After the pins 422, 430 and 432 are fully inserted, and the keyless chuck operation device 30 is properly mounted on the chuck head 31, the tabs 422, 434 and 436 are broken off the corresponding pins 422, 430 and 32, respectively. As shown in FIGS. 34 and 35, the outer surface of the gear 51A includes a recess 440 around the periphery of the hole 284. The diameter of the recess 440 is sufficiently large to receive the head 424 of the locking pin 420 therein. As shown in FIG. 35, the outer surface of the pin head 424 is inside the recess 440 when the pin 420 is fully inserted into the hole 284. After the tabs 422, 434 and 436 are broken off the pins 420, 430 and 432, respectively, the heads of the pins 420, 430 and 432 are generally flush with the surfaces of the corresponding adjacent portions of the cluster gear assemblies 50, 62 and 64, respectively.

Referring to FIGS. 37–40, there is shown an embodiment of the invention that includes the main body 400, the end cap 406 of FIG. 33 and a modified outer shell 450. The outer shell 450 includes three openings 452–454, through which the mounting pins 420, 430 and 432 are inserted for engagement in the cluster gear assemblies 50, 62 and 64. The opening 452 is formed in a "break out" portion 460 of the main body 400. The break out portion 460 is formed by forming an pair of slots 462 and 464 in the upper flange 466. A pair of curved openings 468 and 470 extend from the slots 462 and 464, respectively. The curved openings 468 and 470 extend from points above and to the sides of the opening 452 to a location 472 on the cylindrical sidewall of the main body 400 just below the opening 452. Small portions of the flange 466 and the sidewall portion 472 retain the breakout portion 460 in connection with the rest of the main body 400.

Figure 38:
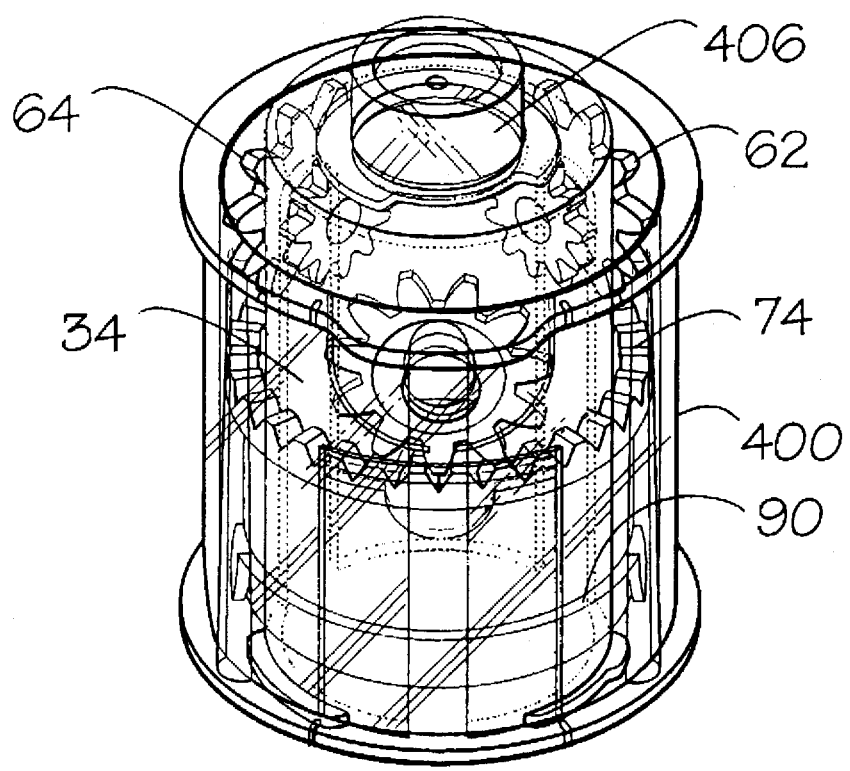
FIG. 38 is a perspective view of the apparatus of FIG. 37 fully assembled and prepared for mounting to a drill chuck head.
Figure 38:
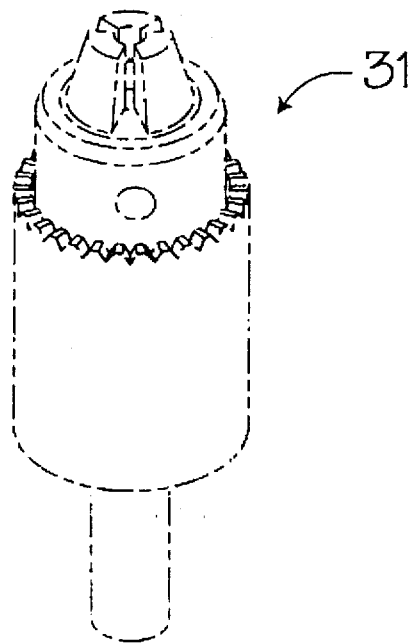

When the keyless chuck operation device 30 is assembled as shown in FIG. 38, it cannot be removed from the chuck head 31 without rendering the keyless chuck operation device 30 inoperable. The heads of the pins 420, 430 and 432 are recessed in the cluster gear assemblies 50, 62 and 64, respectively and covered by the outer shell 450. Therefore, the pins 420, 430 and 432 are not easily removed from the corresponding gear assemblies 50, 62 and 64; and consequently the keyless chuck operation device 30 cannot be easily removed from the chuck head 31. The purpose for preventing the keyless chuck operation device 30 from being removed is to prevent the keyless chuck operation device 30 from being removed and reused after it has become contaminated by use in surgery.

Referring to FIGS. 39 and 40, the break out portion 460 is shown to be removed from the main body 400, which permits the mounting pins 420, 430 and 432 to be removed from the cluster gears assemblies, 50, 62 and 64, respectively. A tool such as a screwdriver or the like may be used to pry the break out portion 460 apart from the main body 450. As shown in FIG. 39, removing the breakout portion 460 from the main body 450 permits access to the heads of the mounting pins 420, 430 and 432 so that they can be pried out of the holes in the gear assemblies 50, 62 and 64 using a sharp object such as the pint of a knife or small screwdriver.

Figure 41:
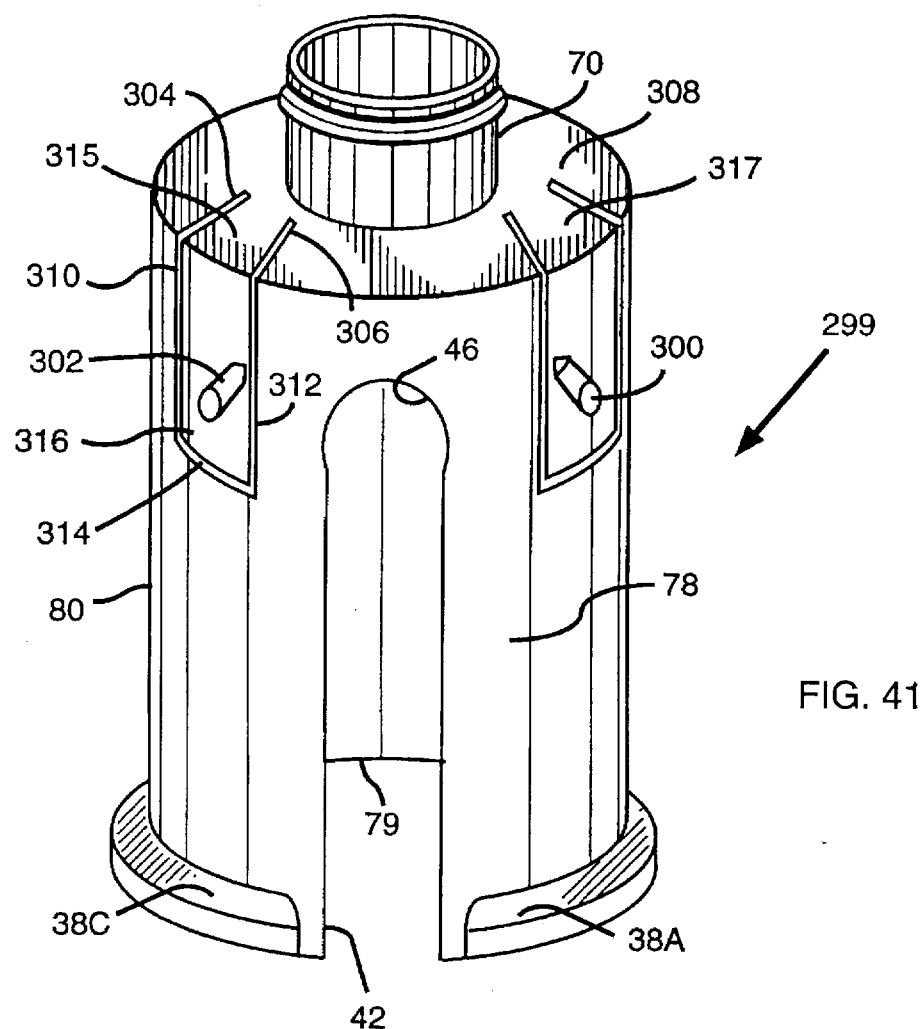
FIG. 41 is a perspective view of an alternative main body.
Figure 42:
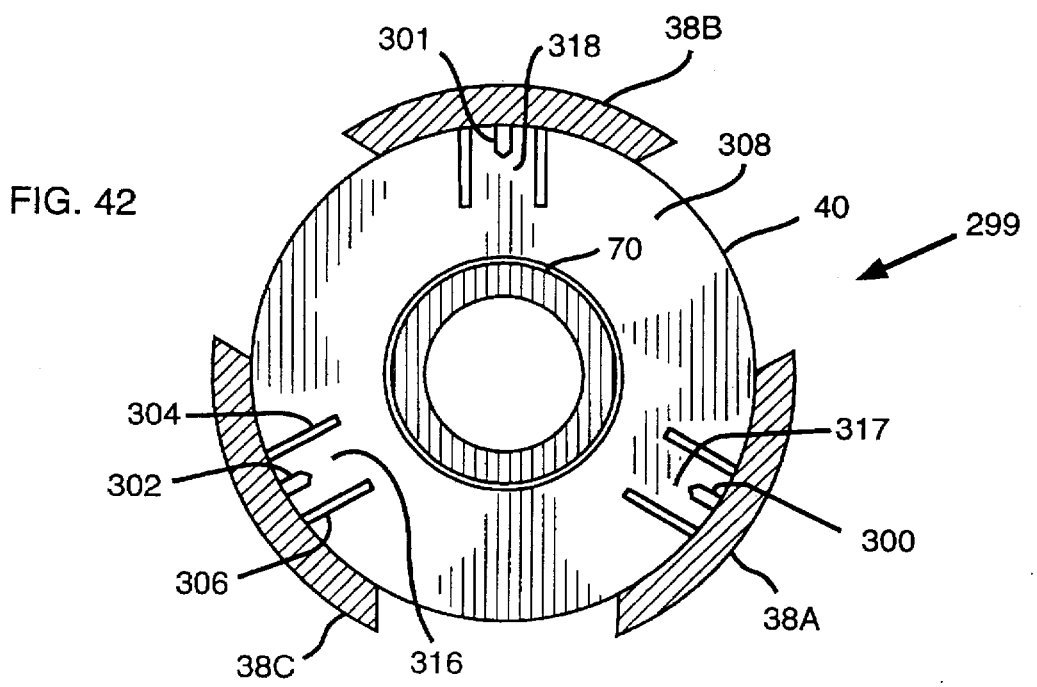
FIG. 42 is a top cross sectional view of the apparatus of FIG. 41.

Referring to FIGS. 41 and 42, the invention may include a main body 299 that includes locking pins 300–302 formed integrally therewith. The locking pins 300–302 are spaced apart by 120° so that they correspond to the holes in the inner cylinder of a standard chuck head. There are a pair of slots 304 and 306 formed in an end face 308 of the main body 32. These slots 304 and 306 extend to the outer periphery of the cylindrical main body 299. A pair parallel of longitudinal slots 310 and 312 extend in the cylindrical surface from the ends of the slots 304 and 306 to a curved slot 314 that extends part of the circumference of the cylinder between the lower ends of the slots 310 and 312.

The portion 316 of the main body 32 bounded by the slots 304, 306, 310, 312 and 314 is deformable because a narrow portion 315 connects the portion 316 to the end face 308. The locking pin 302 is formed in the deformable portion 316. The locking pins 300 and 301 are formed in flexible portions 317 and 318.

As the main body 299 is slid over the chuck head, the ends of the pins 300–302 come into contact with the end of the outer cylinder of the chuck head, which is typically beveled. Advancing the main body upon the chuck head moves the pins 300–302 radially outward. When the pins 300–302 come into alignment with the holes in the inner cylinder, the tensile force caused by the radial deflection of the pins 300–302 causes them to move into the holes in the chuck head. The outer shell 36 is then slid over the ends of the pins. There is a close tolerance between the inner surface of the outer shell 36 and the portion of the main body where the pins 300–302 are formed.

The structures and methods disclosed herein illustrate the principles of the present invention. The invention may be embodied in other specific forms without departing from its spirit or essential characteristics. In particular, the gear arrangements described herein may be modified. An arrangement using worm gears may be used instead of the cluster gear assembly 72. This would allow the keyless chuck operation device 30 to have a smaller diameter than is ordinarily possible with the cluster gears. Instead of having standard gear teeth, the cluster gears may have teeth that are generally spherical which provides smoother operation than is normally achieved with the standard gear teeth as shown herein.

The described embodiments are to be considered in all respects as exemplary and illustrative rather than restrictive. Therefore, the appended claims rather than the foregoing description define the scope of the invention. All modifications to the embodiments described herein that come within the meaning and range of equivalence of the claims are embraced within the scope of the invention.

What is claimed is:

1. Apparatus for keyless opening and closing of the jaws of a drill chuck head having an inner chuck cylinder and an outer chuck cylinder with at least one radial passage in the inner chuck cylinder and a circumferential face gear formed on the outer chuck cylinder, comprising:

a main body formed generally as a hollow cylinder having an open end sized to receive therein the chuck head;

at least one cluster gear assembly rotatably mounted to the main body, the cluster gear assembly having an inner bevel gear arranged to be engaged with the face gear of the chuck head and an outer cluster gear;

a face gear assembly rotatably mounted to the main body, the face gear assembly including a hollow, generally cylindrical gear body formed for receiving the main body therein and including a face gear arranged to be retained in engagement with the outer cluster gear;

an outer shell formed generally as a hollow cylinder and mounted to the face gear assembly so that the main body, the face gear assembly, the outer shell and the chuck head are essentially concentric;

a cam follower connected to an inner surface of the outer shell; and a cam formed in the face gear assembly for selective engagement with the cam follower, the outer shell being movable along a longitudinal axis between a first position where the cam follower engages the cam such that rotating the chuck head opens or closes the jaws of the chuck, depending upon the direction of rotation, and a second position where the chuck head, the main body and the face gear assembly rotate freely within the outer shell.

2. The apparatus of claim 1, further comprising at least one pin extending radially through the side wall of the main body into the radial passage in the chuck head to lock the main body on the chuck.

3. The apparatus of claim 1, further comprising a plurality of pins angularly spaced apart by about 120° and extending radially through the side wall of the main body into the radial passage in the chuck head.

4. The apparatus of claim 1, wherein the main body includes at least one longitudinally aligned slot therein with the cluster gear assembly being mounted in the slot, further comprising:

a shoulder connecting the outer cluster gear and the inner cluster gear together along their longitudinal axes, the shoulder having a longitudinal passage extending therethrough; and a pin extending through the longitudinal passage into the radial passage in the chuck head to lock the cluster gear to the main body.

5. The apparatus of claim 1, wherein the main body includes three longitudinally aligned slots spaced 120° apart, further comprising:

a plurality of cluster gear assemblies mounted in the slots, respectively, each cluster gear assembly including a shaft connecting the outer cluster gears and the corresponding inner cluster gear together along their longitudinal axes, each shaft having a longitudinal passage extending therethrough; and a plurality of pins extending through the longitudinal passages into corresponding radial passages in the chuck head.

6. The apparatus of claim 5, further comprising a flange formed on an end of the main body spaced apart from the cluster gear assemblies, the flange being formed on a portion of the main body that is inwardly deformable so that the gear body may be placed around the main body to engage the face gear with the outer cluster gears, the flange being formed to retain the gear body on the main body such that the gear body is rotatable around the main body.

7. The apparatus of claim 1 wherein the face gear assembly further comprises:

a face gear formed on an upper end of the gear body;

an upper flange formed around the gear body adjacent the face gear; and a central flange formed around the gear body, the central flange including a cam for selective engagement with the detect to open or close the chuck jaws, the cam follower being between the upper flange and the central flange.

8. The apparatus of claim 7 wherein the face gear assembly further comprises:

a lower flange formed on the gear body on the end of the gear body opposite from the face gear; and a keyway extending longitudinally along the outer surface of the gear body between the lower flange and the central flange, the keyway being arranged for alignment with the cam follower to facilitate mounting the outer shell on the face gear assembly.

9. The apparatus of claim 8 wherein the face gear assembly further comprises a wedge formed at the juncture of the keyway and the central flange, the wedge being configured to make the cam follower move radially outward as the outer body is advanced toward its mounting position on the gear body so that the detect may pass over the central flange.

10. The apparatus of claim 8 wherein the face gear assembly further comprises a flattened portion on the edge so that the cam follower may be placed in a pre-load position on the gear body.

11. The apparatus of claim 6 wherein the outer shell includes a flexible sidewall portion that bulges radially outward as the cam follower passes over the central flange of the gear body.

12. The apparatus of claim 6 wherein the cam follower may be placed into contact with the upper flange of the gear body when the outer shell is in its second position.

13. The apparatus of claim 11 wherein the flexible portion includes a passage therein and the cam follower is mounted in the passage.

14. The apparatus of claim 1 wherein a cam follower is formed integrally with the flexible portion.

15. The apparatus of claim 14 wherein the cam follower has a longitudinal slot therein.

16. Apparatus for keyless opening and closing of the jaws of a drill chuck head having at least one radial passage and a circumferential face gear thereon, comprising:

a main body formed generally as a hollow cylinder having an open end sized to receive therein the chuck head;

an outer shell formed generally as a hollow cylinder and mounted to the main body, the outer shell including a free wheeling position in which a person may grasp the outer shell and hold it to guide the drill without causing the chuck jaws to tend to open or close;

a gear drive assembly mounted to the face gear of the chuck; and means for selectively manually engaging the outer shell with the gear drive assembly such that rotating the chuck head opens or closes the jaws of the chuck, depending upon the direction of rotation.

17. Apparatus for keyless opening and closing of the jaws of a drill chuck head having an inner chuck cylinder and an outer chuck cylinder with at least one radial passage in the inner chuck cylinder and a circumferential face gear formed on the outer chuck cylinder, comprising:

a main body formed generally as a hollow cylinder having an open end sized to receive the chuck head therein;

a cluster gear assembly rotatably mounted to the main body, the cluster gear assembly having an inner bevel gear arranged to be engaged with the face gear of the chuck head and an outer cluster gear, the cluster gear assembly including an axial passage therethrough;

a mounting pin arranged to pass through the axial passage in the cluster gear for insertion into the radial passage of the chuck head;

a face gear assembly rotatably mounted to the main body, the face gear assembly including a hollow, generally cylindrical gear body formed for receiving the main body therein and including a face gear arranged to be retained in engagement with the outer cluster gear;

an outer shell formed generally as a hollow cylinder and mounted to the face gear assembly so that the main body, the face gear assembly, the outer shell and the chuck head are essentially concentric;

a cam follower connected to an inner surface of the outer shell; and a cam formed in the face gear assembly for selective engagement with the cam follower, the outer shell being movable along a longitudinal axis between a first position where the cam follower engages the cam such that rotating the chuck head opens or closes the jaws of the chuck, depending upon the direction of rotation, and a second position where the chuck head, the main body and the face gear assembly rotate freely within the outer shell.

18. The keyless chuck operation device of claim 17 wherein the main body includes a radial passage located such that the mounting pin may be passed therethrough into the axial passage of the cluster gear assembly and wherein the mounting pin includes a removable tab for use in inserting the mounting pin in the axial passage of the cluster gear assembly.

19. The keyless chuck operation device of claim 18 wherein the radial passage in the main body is formed in a portion of the main body that is removable to provide access to the mounting pin so that it may removed from the cluster gear assembly to dismount the keyless chuck operation device from the chuck head.

20. The keyless chuck operation device of claim 17, further comprising an end cap mounted to the main body, the end cap being formed generally as a cylindrical body closed at one end and open at the other end and having a flange around the open end, the end cap being arranged for insertion into the lower open end of the main body such that the cylindrical portion of the end cap extends from an opening in the upper end of the main body with the flange on the end cap being retained inside the main body in engagement with an inner portion of the upper end of the main body.

21. Apparatus for keyless opening and closing of the jaws of a drill chuck head having at least one radial passage and a circumferential face gear thereon, comprising:

a main body formed generally as a hollow cylinder having an open end sized to receive therein the chuck head, the main body including a locking pin formed integrally therewith for locking the main body to the chuck head;

an outer shell formed generally as a hollow cylinder and mounted to the main body;

a gear drive assembly mounted to the face gear of the chuck; and means for selectively manually engaging the outer shell with the gear drive assembly such that rotating the chuck head opens or closes the jaws of the chuck, depending upon the direction of rotation.

22. The apparatus of claim 21 wherein the locking pin is mounted on a deformable portion of the main body.

23. The apparatus of claim 1, further comprising means for preventing the cam follower from becoming inadvertently engaged with the cam.

* * * * *